(12) United States Patent
Hall et al.

(10) Patent No.: US 7,459,541 B2
(45) Date of Patent: Dec. 2, 2008

(54) MATRIX-TARGETED FUSION POLYPEPTIDES FOR TISSUE REGENERATION AND WOUND HEALING

(75) Inventors: Frederick L. Hall, Glendale, CA (US); Erlinda M. Gordon, Glendale, CA (US); Robert W. Beart, Pasadena, CA (US); Marcel Nimni, Santa Monica, CA (US)

(73) Assignee: University of Southern California, Los Angeles, CA (US)

( * ) Notice: Subject to any disclaimer, the term of this patent is extended or adjusted under 35 U.S.C. 154(b) by 612 days.

(21) Appl. No.: 10/733,852

(22) Filed: Dec. 10, 2003

(65) Prior Publication Data
US 2005/0037469 A1 Feb. 17, 2005

Related U.S. Application Data

(63) Continuation of application No. 09/624,874, filed on Jul. 21, 2000, now abandoned.

(60) Provisional application No. 60/145,488, filed on Jul. 21, 1999.

(51) Int. Cl.
*C07K 14/475* (2006.01)
*C07K 14/48* (2006.01)
*C07K 14/62* (2006.01)
*C07K 14/71* (2006.01)

(52) U.S. Cl. .................. 530/399; 530/350; 530/356; 530/402; 536/23.4; 435/69.7

(58) Field of Classification Search .................... None
See application file for complete search history.

(56) References Cited

U.S. PATENT DOCUMENTS

| | | | |
|---|---|---|---|
| 4,980,289 A * | 12/1990 | Temin et al. | 435/235.1 |
| 5,704,910 A | 1/1998 | Humes | 604/52 |
| 6,004,798 A | 12/1999 | Anderson et al. | |
| 6,387,663 B1 * | 5/2002 | Hall et al. | 435/69.7 |
| 6,955,898 B2 * | 10/2005 | Hall et al. | 435/69.1 |
| 2002/0102709 A1 * | 8/2002 | Ishikawa et al. | 435/226 |
| 2005/0250936 A1 * | 11/2005 | Oppermann et al. | 530/399 |

FOREIGN PATENT DOCUMENTS

| | | |
|---|---|---|
| WO | WO 96/25179 | 8/1996 |
| WO | WO 96/39430 | 12/1996 |
| WO | WO 98/44938 | 10/1998 |

OTHER PUBLICATIONS

Carlini et al. Effect of recombinant human erythropoietin on endothelial cell apoptosis. Kidney International vol. 55, pp. 546-553 (1999).*
Dale et al. Compartment switching of WNT-2 expression in human breast tumors. Cancer research 56 4320-4323, Oct. 1, 1996.*
Kurada et al. Epidermal growth factor receptor:its role in Drosophila eye differentiation and cell survival. Apoptosis 4:239-243 (1999).*
Han et al., "Refolding of a Recombinant Collagen-Targeted TGF-β2 Fusion Protein Expressed in *Escherichia coli*," Protein Expression and Purification, vol. 11, p. 169-178 (1997).
Nishi et al., "Collagen-binding growth factors: Production and characterization of functional fusion proteins having a collagen-binding domain," Proc. Natl. Acad. Sci. USA, vol. 95, p. 7018-7023 (1998).
Gordon et al., "Capture and Expansion of Bone Marrow-Derived Mesenchymal Progenitor Cells with a Transforming Growth Factor-β1-von Willebrand's Factor Fusion Protein for Retrovirus-Mediated Delivery of Coagulation Factor IX," Human Gene Therapy, vol. 8, p. 1385-1394 (1997).
Hall et al., "Targeting Retroviral Vectors to Vascular Lesions by Genetic Engineering of the MoMLV gp70 Envelope Protein," Human Gene Therapy, vol. 8, p. 2183-2192 (1997).

* cited by examiner

*Primary Examiner*—Marianne P Allen
*Assistant Examiner*—Regina M DeBerry
(74) *Attorney, Agent, or Firm*—Fish & Richardson P.C.

(57) ABSTRACT

The present invention relates to compositions and methods for promoting tissue repair and regeneration. The invention provides a fusion polypeptide useful for targeting tissues for regeneration and methods of use therefore.

2 Claims, 7 Drawing Sheets

P1 (EGF Sense Primer)

```
         | NDE1
5'   t ata cat atg aga aat agt gac tct gaa
             M   R   N   S   D   S   E
```

P2 (EGF Antisense Primer)

```
                              | ECOR1
5'       cac gct ggc cac ggg aat tcg a
3'       gtg cga ccg gtg ccc tta agc t
          H   A   G   H   G
```

P3 (CBD Sense Primer)

```
         | ECOR1
5'   tgg gag aat tcg ggc cat atg tgg cgc
                            M   W   R
```

P4 (CBD Antisense Primer)

```
                              | HIND III
5'       t ctg agc ggt gct ccc aag ctt gcg
3'       a gac tcg cca cga ggg ttc gaa cgc
          L   S   G   A   P
```

Figure 4

Binding of EGF-vWF Fusion Proteins to Collagen Matrices

SEQUENCE LISTING

```
<160> NUMBER OF SEQ ID NOS: 12

<210> SEQ ID NO 1
<211> LENGTH: 10
<212> TYPE: PRT
<213> ORGANISM: Bos taurus

<400> SEQUENCE: 1

Trp Arg Glu Pro Ser Phe Met Ala Leu Ser
 1               5                  10

<210> SEQ ID NO 2
<211> LENGTH: 28
<212> TYPE: DNA
<213> ORGANISM: Artificial Sequence
<220> FEATURE:
<223> OTHER INFORMATION: Sense primer
<220> FEATURE:
<221> NAME/KEY: CDS
<222> LOCATION: (8)...(28)

<400> SEQUENCE: 2 tatacat atg aga aat agt gac tct gaa                                    28
        Met Arg Asn Ser Asp Ser Glu
         1               5

<210> SEQ ID NO 3
<211> LENGTH: 7
<212> TYPE: PRT
<213> ORGANISM: Artificial Sequence
<220> FEATURE:
<223> OTHER INFORMATION: Syntheticaly generated peptide

<400> SEQUENCE: 3

Met Arg Asn Ser Asp Ser Glu
```

```
                                 1               5

<210> SEQ ID NO 4
<211> LENGTH: 22
<212> TYPE: DNA
<213> ORGANISM: Artificial Sequence
<220> FEATURE:
<223> OTHER INFORMATION: Sense primer
<220> FEATURE:
<221> NAME/KEY: CDS
<222> LOCATION: (1)...(15)

<400> SEQUENCE: 4 cac gct ggc cac ggg aattcga                                              22
His Ala Gly His Gly
  1               5

<210> SEQ ID NO 5
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 5

His Ala Gly His Gly
  1               5

<210> SEQ ID NO 6
<211> LENGTH: 22
<212> TYPE: DNA
<213> ORGANISM: Artificial Sequence
<220> FEATURE:
<223> OTHER INFORMATION: Antisense primer

<400> SEQUENCE: 6
tcgaattccc gtggccagcg tg                                                 22

<210> SEQ ID NO 7
<211> LENGTH: 27
<212> TYPE: DNA
<213> ORGANISM: Artificial Sequence
<220> FEATURE:
<223> OTHER INFORMATION: Sense primer
<220> FEATURE:
<221> NAME/KEY: CDS
<222> LOCATION: (19)...(27)

<400> SEQUENCE: 7
tgggagaatt cgggccat atg tgg cgc                                          27
                    Met Trp Arg
                      1

<210> SEQ ID NO 8
<211> LENGTH: 3
<212> TYPE: PRT
<213> ORGANISM: Artificial Sequence
<220> FEATURE:
<223> OTHER INFORMATION: Synthetically generated peptide

<400> SEQUENCE: 8

Met Trp Arg
  1

<210> SEQ ID NO 9
<211> LENGTH: 25
<212> TYPE: DNA
<213> ORGANISM: Artificial Sequence
```

```
<220> FEATURE:
<223> OTHER INFORMATION: Sense primer
<220> FEATURE:
<221> NAME/KEY: CDS
<222> LOCATION: (2)...(16)

<400> SEQUENCE: 9 t ctg agc ggt gct ccc aagcttgcg                          25
  Leu Ser Gly Ala Pro
   1               5

<210> SEQ ID NO 10
<211> LENGTH: 5
<212> TYPE: PRT
<213> ORGANISM: Artificial Sequence
<220> FEATURE:
<223> OTHER INFORMATION: Syntheticaly generated peptide

<400> SEQUENCE: 10

Leu Ser Gly Ala Pro
 1               5

<210> SEQ ID NO 11
<211> LENGTH: 25
<212> TYPE: DNA
<213> ORGANISM: Artificial Sequence
<220> FEATURE:
<223> OTHER INFORMATION: Antisense primer

<400> SEQUENCE: 11
cgcaagcttg ggagcaccgc tcaga                              25

<210> SEQ ID NO 12
<211> LENGTH: 17
<212> TYPE: PRT
<213> ORGANISM: Bos taurus

<400> SEQUENCE: 12

His Val Gly Trp Arg Glu Pro Ser Phe Cys Ala Leu Ser Cys Pro His
 1               5                  10                  15
Gly
```

MATRIX-TARGETED FUSION POLYPEPTIDES FOR TISSUE REGENERATION AND WOUND HEALING

CROSS REFERENCE TO RELATED APPLICATIONS

This application is a continuation (and claims the benefit of priority under 35 USC 120) of U.S. application Ser. No. 09/624,874, filed Jul. 21, 2000, now abandoned which claims priority to U.S. provisional application Ser. No. 60/145,488, filed Jul. 21, 1999. The disclosure of the prior applications are considered part of (and are incorporated by reference in) the disclosure of this application.

TECHNICAL FIELD

The present invention relates generally to pharmaceutical agents targeted to a tissue for promoting tissue regeneration, and more particularly to the use of collagen-binding domains to target a growth factor to a desired tissue.

BACKGROUND

Impaired tissue healing is a significant problem in health care. Chronic, non-healing wounds are a major cause of prolonged morbidity in the aged human population. Tissue repair is particularly relevant to bedridden or diabetic patients who develop severe, external, non-healing skin ulcers. In addition, those patients suffering from internal lesions, such as those associated with disorders of the digestive tract, are particularly susceptible to the effects of non or slow-healing tissue damage.

Pharmaceutical agents that promote tissue regeneration at the site of a lesion, such as growth factors, have been utilized to accelerate wound repair. Growth factors are molecules that function not only as growth simulators (mitogens), but also as growth inhibitors. Growth factors are also known to stimulate cell migration (e.g., mitogenic cytokines), function as chemotactic agents, inhibit cell migration or invasion of tumor cells, modulate differentiated functions of cells, be involved in apoptosis, and promote survival of cells. For example, epidermal growth factor (EGF) is a mitogen that not only effects suppression of gastric acid secretion and fetal lung development, but also effects wound healing and epidermal regeneration (Franklin et al., J. Lab. Clin. Med., 108:103, 1985). EGF has been shown to be a potent stimulator of epithelial cell proliferation in the human intestine (Alison et al., Cell Biol. Int., 18:1, 1994) and other tissues.

Previous studies have demonstrated the viability of targeting extracellular matrix molecules, such as exposed collagen, for delivery of a pharmaceutical agent to a specific tissue. For example, von Willebrand Factor (vWF)-derived collagen-binding domains have been used to target the TGF-$\beta$ family of growth factors to damaged tissue (Tuan et al., Conn. Tiss. Res., 34:1, 1996; Han et al., Protein Expr. Purif., 11:169, 1997).

Pharmaceutical agents that promote tissue regeneration are useful not only for treating disorders associated with impaired tissue regeneration, but also for promoting tissue regeneration associated with surgical procedures, for example. Several strategies have been developed to accomplish enhanced tissue repair for the treatment of damaged tissue. Within these strategies, there is a need for the controlled, sustained, site-specific targeting of a pharmaceutical agent to a wound site for the purpose of promoting tissue regeneration.

SUMMARY

The present invention provides new compositions and methods to induce therapeutic repair of epithelial tissue by specifically targeting tissue in need of such repair with a fusion polypeptide of the invention. The invention promotes localized wound healing by providing a cell proliferation-modulating agent fused to a collagen-binding domain. The new compositions and methods are useful for wound healing in general and for promoting repair of colonic lesions, for the capture and expansion of crypt stem cells, and the enhancement of retroviral gene transfer in colonic mucosal cells, in particular.

In one embodiment, a fusion polypeptide comprising an epithelial cell proliferation-modulating agent and a collagen-binding domain capable of binding to collagen, is provided. A nucleic acid sequence encoding the fusion polypeptide is also provided.

In another aspect, the invention provides a method of producing a fusion polypeptide of the invention having a collagen-binding domain and an epithelial cell proliferation-modulating agent, by growing the host cells containing a nucleic acid encoding the fusion polypeptide under conditions that allow expression of the nucleic acid sequence and recovering the fusion polypeptide.

In another embodiment, the invention provides method for modulating epithelial cell proliferation in a subject. In one aspect, the modulating is by administering to the subject a fusion polypeptide comprising a collagen-binding domain source linked to an epithelial cell proliferation-modulating agent. In another aspect, the modulating is by administering to the subject a therapeutically effective amount of a nucleic acid sequence encoding a fusion polypeptide comprising a collagen-binding domain linked to an epithelial cell proliferation-modulating agent.

In a further embodiment, a tissue graft, comprising isolated tissue comprising epithelial cells treated with a fusion polypeptide comprising a collagen-binding domain linked to an epithelial cell proliferation-modulating agent, is provided. Also provided is a method of preparing a tissue graft using an effective amount of a fusion polypeptide of the invention.

The invention further provides a method for modulating tissue regeneration in a subject. In one aspect, the method comprises administering to the subject a therapeutically effective amount of a fusion polypeptide of the invention. In another aspect, the method comprises administering to the subject a therapeutically effective amount of a nucleic acid encoding a fusion polypeptide of the invention.

In another embodiment, the invention provides a pharmaceutical composition for promoting tissue repair. In one aspect, the composition comprises a fusion polypeptide comprising a collagen-binding domain linked to an epithelial cell proliferation-modulating agent in a pharmaceutically acceptable carrier. In another aspect, the composition comprises a nucleic acid encoding a fusion polypeptide of the invention.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 4 shows binding of EGF and EGF-CBD fusion protein to collagen matrices. Immunoreactive EGF is depicted as dark staining material in standard ELISA wells, and the collagen-binding affinities were measured using a Rainbow Spectra Elisa reader and expressed as O.D. readings at A650 (plotted on the vertical axis).

FIG. 5 is a graph showing the results of a biologic assay for EGF activity. The biologic activities of the collagen-targeted (rEGF-CBD; black vertical bars) and non-targeted EGF (rEGF; white vertical bars) were compared to that of commercial EGF. Proliferation of NIH3T3 cells was measured by BrdU incorporation during DNA synthesis, in response to treatment with the respective EGF preparation, and plotted on the vertical axis as O.D. readings at 620 nm.

FIG. 6 shows in vivo binding of EGF-CBD to exposed collagen in a nude mouse model of ulcerative colitis. Panels A and B: Mason trichrome stain of exposed collagen (blue-staining material) in areas of inflamed colon induced by rectal instillation of a 5% acetic acid solution. Panels C and D: Binding of EGF-CBD to exposed collagen in areas of inflamed colon as indicated by positive immunostaining (reddish-brown-staining material) using a primary antibody directed against the His×6 tag. Panel E: Negative binding of EGF without the collagen-binding domain; Panel F: Negative PBS control.

FIG. 7 shows comparative efficacy of a collagen-targeted vs. non-targeted EGF in a mouse model of experimental colitis. The histologic features of colitis (seen as edema, hemorrhage, erosion, ulceration) three days after treatment with (Panels A-B) PBS, (Panels C-D) EGF and (Panels E-F) EGF-CBD-treated mice are shown (100× magnification).

Like reference symbols in the various drawings indicate like elements.

DETAILED DESCRIPTION

The present invention provides a recombinant fusion polypeptide comprising EGF and an appropriate collagen-binding domain (CBD) for enhancing the effective local concentration of EGF at the site of tissue injury thereby promoting repair of damaged intestinal mucosa in animal models and, ultimately, in humans. Thus, the present invention provides a fusion polypeptide bearing an auxiliary collagen-binding domain derived from coagulation von Willebrand factor (vWF) linked to to an epithelial cell proliferation-modulating agent. The invention further provides methods for using the fusion polypeptide in stimulating cell proliferation in vitro and promoting healing in vivo in an animal model.

In one embodiment, a fusion polypeptide including an epithelial cell proliferation-modulating agent and a collagen-binding domain capable of binding to collagen, is provided. A nucleic acid sequence encoding the fusion polypeptide is also provided.

A "fusion polypeptide," as used herein, is a polypeptide containing portions of amino acid sequence derived from two or more different proteins, or two or more regions of the same protein that are not normally contiguous. A "collagen-binding domain" is any polypeptide, or portion thereof, that can bind collagen. Several collagen-binding domains are known in the art (Cruz, M. A. et al., J. Biol. Chem., 270:10822, 1995; Hoylaerts, M. F. et al., Biochem. J., 324:185, 1997; Lankhof, H. et al., Thrombos Haemostas, 75;950, 1996). In one embodiment, the collagen-binding domain is the collagen-binding domain of von Willebrand factor, which is involved in the recognition of exposed vascular collagen (Takagi, J. et al., Biochemistry 32:8530, 1992; Tuan, T. L. et al., Conn. Tiss. Res., 34:1, 1996; Gordon, E. M. et al., Hum. Gene Ther., 8:1385, all herein incorporated by reference). von Willebrand factor was initially identified as a hemostatic factor in studies of inherited hemophilias (Wagner, Ann., Rev. Cell. Biol., 6:217, 1990), and has been shown to perform a vital surveillance function by targeting platelet aggregates to vascular lesions (Ginsburg and Bowie, Blood, 79:2507, 1992). The decapeptide WREPSFMALS (SEQ ID NO:1) has been identified to be key in the binding of von Willebrand's factor to collagen (Takagi, J. et al., supra, 1992; Tuan, T. L. et al., supra, 1996). Assays to identify collagen-binding domains of use in the subject invention are known in the art (Takagi, J. et al., supra, 1992; Tuan, T. L. et al., supra, 1996).

As used herein, an "epithelial cell proliferation-modulating agent" is any agent that can promote or inhibit epithelial cell growth or differentiation. Preferably, an epithelial cell proliferation-modulating agent of the invention is a polypeptide. More preferably, the polypeptide is a fusion polypeptide comprising a collagen-binding domain and a growth factor, or active fragment thereof.

The term "growth factor," as used herein, includes those molecules that function as growth simulators (mitogens) or as growth inhibitors (sometimes referred to as negative growth factors). Growth factors are also known to stimulate cell migration (e.g., mitogenic cytokines), function as chemotactic agents, inhibit cell migration or invasion of tumor cells, modulate differentiated functions of cells, be involved in apoptosis, and promote survival of cells. Such factors can be secreted as diffusible factors and can also exist in membrane-anchored forms. They can, therefore, act in an autocrine, paracrine, juxtacrine, or retrocrine manner. A cytokine is one type of growth factor. A "cytokine" is polypeptide that acts as a humoral regulator at nano-to-picomolar concentrations and which, either under normal or pathological conditions, can modulate the functional activities of individual cells and tissues. A cytokine can mediate interactions between cells directly and/or can regulate processes taking place in the extracellular environment. Cytokines comprise interleukins, lymphokines, monokines, interferons, colony-stimulating factors, and chemokines, in addition to a variety of other proteins.

Growth factors further include epidermal growth factors (EGFs), transforming growth factors (TGFs), platelet-derived growth factors (PDGFs), fibroblast growth factors (FGFs), hepatocyte growth factors (HGFs), hemopoietic growth factors (HeGFs), tumor necrosis factor (TNF-alpha), platelet-derived endothelial cell growth factor (PD-ECGF), insulin-like growth factor (IGF), interleukin-8, growth hormone, angiopoietin, vascular endothelial growth factor (VEGF), acidic and basic fibroblast growth factors (FGFs), transforming growth factor alpha (TGF-α), and CYR 61 (Babic et al., Proc. Natl. Acad. Sci. USA, 95:6355, 1998; Kireeva et al., Mol. Cell. Biol., 16:1326, 1996). Such factors further include insulin, IGF-I, IGF-II, nerve growth factor, NGF receptor, EGF, TGF-β, EGF receptor, neu, TGF-β1, TGF-β2, TGF-β3, inhibin α, inhibin β, Mullerian inhibitory substance, TNF-α/β, TNF-receptor (type 1), TNF-receptor (type 2), PDGF A-chain, PDGF B-chain, PDGF receptor α, PDGF receptor β, a-FGF, b-FGF, wnt-2, hst/ks3, hepatocyte growth factor, HGF receptor (c-met), IL-1α/β, (α-chains) IL-2, IL-3, IL-4, IL-5, IL-6, IL-7, IL-9, IL-11, IL-12A (p35), IL-12B (p40), Interleukin 1 (type 1), Interleukin-2α, Interleukin-2β, Interleukin-4, Interleukin-5α, Interleukin-6, Interleukin-7, M-CSF (also called CSF-1), M-CSF receptor (c-fms), GM-CSF, GM-CSF receptor α, GM-CSF receptor β, G-CSF, G-CSF receptor, stem cell factor, SCF receptor (c-kit), Erythropoietin (epo), epo receptor, and Leukemia inhibitory factor. Each of these molecules has been shown to induce cell proliferation, cell growth or differentiation in vivo. Other similar molecules that display cell growth or differentiation modulating activity are the heparin binding growth factors (HBGFs).

Figure 1:
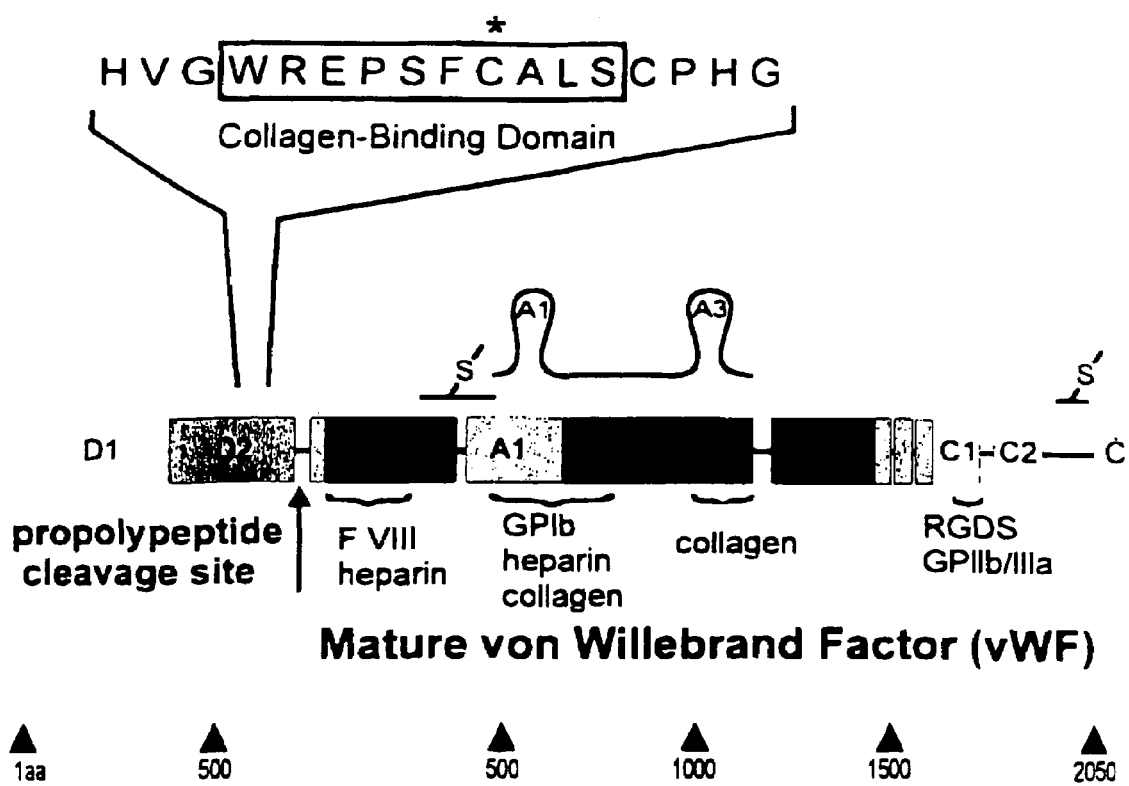
FIG. 1 is a diagram showing the structural domains of von Willebrand Factor. The A1 loop within the mature polypeptide encompasses the GP1b, collagen and heparin binding domains that function to promote platelet adhesion, collagen binding and heparin binding. The minimal collagen binding sequences of human and bovine vWF, including the flanking residues, are shown (SEQ ID NO: 12).

Epidermal growth factor (EGF) is a mitogen that can effect, for example, suppression of gastric acid secretion, fetal lung development, wound healing, and epidermal regeneration. Given the distribution and physiological responses to EGF, it appears that EGF serves to ensure the integrity and renewal of epithelial cell populations in the body. In the human gastrointestinal tract, chronic mucosal ulceration has been shown to induce the formation of a unique EGF secreting cell lineage (putative intestinal stem cells) from the base of the intestinal crypts (Wright et al., Nature, 343:82, 1990), and this EGF-secreting gland was found only in the mucosa adjacent to the site of the ulceration. Thus, EGF is linked conceptually to colonic stem cell activity and, subsequently, to wound healing.

As used herein, the term "nucleic acid sequence" refers to a polymer of deoxyribonucleotides or ribonucleotides in the form of a separate fragment or as a component of a larger construct. Nucleic acids expressing the products of interest can be assembled from cDNA fragments or from oligonucleotides that provide a synthetic gene which is capable of being expressed in a recombinant transcriptional unit. Polynucleotide or nucleic acid sequences of the invention include DNA, RNA, and cDNA sequences.

Nucleic acid sequences utilized in the invention can be obtained by several methods. For example, the DNA can be isolated using hybridization procedures that are well known in the art. These include, but are not limited to:

(1) hybridization of probes to genomic or cDNA libraries to detect shared nucleotide sequences; (2) antibody screening of expression libraries to detect shared structural features; and (3) synthesis by the polymerase chain reaction (PCR). Sequences for specific genes can also be found in GenBank, National Institutes of Health computer database.

In another aspect, the invention provides a method of producing a fusion polypeptide of the invention having a collagen-binding domain and an epithelial cell proliferation-modulating agent, by growing the host cells containing a nucleic acid encoding the fusion polypeptide under conditions that allow expression of the nucleic acid sequence, and recovering the fusion polypeptide. The nucleic acid sequence of the invention can be operably linked to a promoter for expression in a prokaryotic or eukaryotic expression system. For example, a nucleic acid of the invention can be incorporated in an expression vector. Delivery of a nucleic acid of the invention can be achieved by introducing the nucleic acid into a cell using a variety of methods known to those of skill in the art. For example, the construct can be delivered into a cell using a colloidal dispersion system. Alternatively, nucleic acid construct of the invention can be incorporated (i.e., cloned) into an appropriate vector. For purposes of expression, the nucleic acid sequences encoding the fusion polypeptide of the invention may be inserted into a recombinant expression vector. The term "recombinant expression vector" refers to a plasmid, virus, or other vehicle known in the art that has been manipulated by insertion or incorporation of the nucleic acid sequences encoding the fusion polypeptides of the invention. The expression vector typically contains an origin of replication, a promoter, as well as specific genes that allow phenotypic selection of the transformed cells. Vectors suitable for use in the present invention include, but are not limited to, the T7-based expression vector for expression in bacteria (Rosenberg et al., Gene, 56:125, 1987), the PMSXND expression vector for expression in mammalian cells (Lee and Nathans, J. Biol. Chem., 263:3521, 1988), baculovirus-derived vectors for expression in insect cells, cauliflower mosaic virus, CaMV, tobacco mosaic virus, TMV. Depending on the vector utilized, any of a number of suitable transcription and translation elements, including constitutive and inducible promoters, transcription enhancer elements, transcription terminators, etc. may be used in the expression vector (see, e.g., Bitter et al., Methods in Enzymology, 153:516-544, 1987). These elements are well known to one of skill in the art.

The term "operably linked" or "operably associated" refers to functional linkage between the regulatory sequence and the nucleic acid sequence regulated by the regulatory sequence. The operably linked regulatory sequence controls the expression of the product expressed by the nucleic acid sequence. Alternatively, the functional linkage also includes an enhancer element.

"Promoter" means the minimal nucleotide sequence sufficient to direct transcription. Also included in the invention are those promoter elements that are sufficient to render promoter-dependent nucleic acid sequence expression controllable for cell-type specific, tissue specific, or inducible by external signals or agents; such elements may be located in the 5' or 3' regions of the native gene, or in the introns.

"Gene expression" or "nucleic acid sequence expression" means the process by which a nucleotide sequence undergoes successful transcription and translation such that detectable levels of the delivered nucleotide sequence are expressed in an amount and over a time period so that a functional biological effect is achieved.

In yeast, a number of vectors containing constitutive or inducible promoters may be used. (Current Protocols in Molecular Biology, Vol. 2, Ed. Ausubel et al., Greene Publish. Assoc. & Wiley Interscience, Ch. 13, 1988; Grant et al., "Expression and Secretion Vectors for Yeast," in Methods in Enzymology, Eds. Wu & Grossman, Acad. Press, N.Y., Vol. 153, pp.516-544, 1987; Glover, DNA Cloning, Vol. II, IRL Press, Wash., D.C., Ch. 3, 1986; "Bitter, Heterologous Gene Expression in Yeast," Methods in Enzymology, Eds. Berger & Kimmel, Acad. Press, N.Y., Vol. 152, pp. 673-684, 1987; and The Molecular Biology of the Yeast Saccharomyces, Eds. Strathern et al., Cold Spring Harbor Press, Vols. I and II, 1982). A constitutive yeast promoter, such as ADH or LEU2, or an inducible promoter, such as GAL, may be used ("Cloning in Yeast," Ch. 3, R. Rothstein In: DNA Cloning Vol.11, A Practical Approach, Ed. DM Glover, IRL Press, Wash., D.C., 1986). Alternatively, vectors may be used which promote integration of foreign DNA sequences into the yeast chromosome.

An expression vector of the invention can be used to transform a target cell. By "transformation" is meant a permanent genetic change induced in a cell following incorporation of new DNA (i.e., DNA exogenous to the cell). Where the cell is a mammalian cell, the permanent genetic change is generally achieved by introduction of the DNA into the genome of the cell. By "transformed cell" is meant a cell into which (or into an ancestor of which) has been introduced, by means of recombinant DNA techniques, a DNA molecule encoding a fusion protein consisting of a collagen-binding domain linked to an epithelial cell proliferation-modulating agent, or fragment thereof. Transformation of a host cell with recombinant DNA may be carried out by conventional techniques as are well known to those skilled in the art. Where the host is prokaryotic, such as $E.\ coli$, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

A fusion polypeptide of the invention can be produced by expression of nucleic acid encoding the protein in prokaryotes. These include, but are not limited to, microorganisms, such as bacteria transformed with recombinant bacteriophage DNA, plasmid DNA, or cosmid DNA expression vectors encoding a fusion protein of the invention. The constructs can be expressed in $E.\ coli$ in large scale for in vitro assays. Purification from bacteria is simplified when the sequences include tags for one-step purification by nickel-chelate chromatography. The construct can also contain a tag to simplify isolation of the fusion polypeptide. For example, a polyhistidine tag of, e.g., six histidine residues, can be incorporated at the amino terminal end of the fluorescent protein. The polyhistidine tag allows convenient isolation of the protein in a single step by nickel-chelate chromatography. The fusion polypeptide of the invention can also be engineered to contain a cleavage site to aid in protein recovery. Alternatively, the fusion polypeptides of the invention can be expressed directly in a desired host cell for assays in situ.

When the host is a eukaryote, such methods of transfection of DNA as calcium phosphate co-precipitates, conventional mechanical procedures, such as microinjection, electroporation, insertion of a plasmid encased in liposomes, or virus vectors may be used. Eukaryotic cells can also be cotransfected with DNA sequences encoding the fusion polypeptide of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982). Preferably, a eukaryotic host is utilized as the host cell, as described herein.

Eukaryotic systems, and preferably mammalian expression systems, allow for proper post-translational modifications of expressed mammalian proteins to occur. Eukaryotic cells that possess the cellular machinery for proper processing of the primary transcript, glycosylation, phosphorylation, and advantageously secretion of the gene product should be used as host cells for the expression of the polypeptide of the invention. Such host cell lines may include, but are not limited to, CHO, VERO, BHK, HeLa, COS, MDCK, Jurkat, HEK-293, and WI38.

For long-term, high-yield production of recombinant proteins, stable expression is preferred. Rather than using expression vectors that contain viral origins of replication, host cells can be transformed with the cDNA encoding a fusion protein of the invention controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci that, in turn, can be cloned and expanded into cell lines. For example, following the introduction of foreign DNA, engineered cells may be allowed to grow for 1-2 days in an enriched media, and then are switched to a selective media. A number of selection systems may be used, including, but not limited to, the herpes simplex virus thymidine kinase (Wigler et al., Cell, 11:223, 1977), hypoxanthine-guanine phosphoribosyltransferase (Szybalska & Szybalski, Proc. Natl. Acad. Sci. USA, 48:2026, 1962), and adenine phosphoribosyltransferase (Lowy et al., Cell, 22:817, 1980) genes can be employed in tk-, hgprt- or aprt- cells, respectively. Also, antimetabolite resistance can be used as the basis of selection for dhfr, which confers resistance to methotrexate (Wigler et al., Proc. Natl. Acad. Sci. USA, 77:3567, 1980; O'Hare et al., Proc. Natl. Acad. Sci. USA, 8:1527, 1981); gpt, which confers resistance to mycophenolic acid (Mulligan & Berg, Proc. Natl. Acad. Sci. USA, 78:2072, 1981; neo, which confers resistance to the aminoglycoside G-418 (Colberre-Garapin et al., J. Mol. Biol., 150:1, 1981); and hygro, which confers resistance to hygromycin genes (Santerre et al., Gene, 30:147, 1984). Recently, additional selectable genes have been described, namely trpB, which allows cells to utilize indole in place of tryptophan; hisD, which allows cells to utilize histinol in place of histidine (Hartman & Mulligan, Proc. Natl. Acad. Sci. USA, 85:8047, 1988); and ODC (ornithine decarboxylase), which confers resistance to the ornithine decarboxylase inhibitor, 2-(difluoromethyl)-DL-ornithine, DFMO (McConlogue L., In: Current Communications in Molecular Biology, Cold Spring Harbor Laboratory, ed., 1987).

Techniques for the isolation and purification of either microbially or eukaryotically expressed polypeptides of the invention may be by any conventional means, such as, for example, preparative chromatographic separations and immunological separations, such as those involving the use of monoclonal or polyclonal antibodies or antigen.

A nucleic acid encoding a fusion polypeptide of the invention can also be used for gene therapy purposes. For example, when treating disorders associated with chronic impaired tissue regeneration, it may be desirable to provide such tissues with a means for endogenously expressing the fusion polypeptide of the invention.

Numerous gene therapy methods that take advantage of retroviral vectors for treating a wide variety of diseases are known in the art (see, e.g., U.S. Pat. Nos. 4,405,712 and 4,650,764; Friedmann, Science, 244:1275-1281, 1989; Mulligan, Science, 260:926-932, 1993; and Crystal, R., Science 270:404-410, 1995, each of which are incorporated herein by reference in their entirety). An increasing number of these methods are currently being applied in human clinical trials (Morgan, 1993, BioPharm, 6(1):32-35; see also The Development of Human Gene Therapy, Theodore Friedmann, Ed., Cold Spring Harbor Laboratory Press, Cold Spring Harbor, N.Y., 1999; and ISBN 0-87969-528-5, which are incorporated herein by reference in their entirety).

Another targeted delivery system useful for introducing a nucleic acid of the invention into a target cell is a colloidal dispersion system. Colloidal dispersion systems include macromolecule complexes, nanocapsules, microspheres, beads, and lipid-based systems, including oil-in-water emulsions, micelles, mixed micelles, and liposomes. The preferred colloidal system of this invention is a liposome. Liposomes are artificial membrane vesicles that are useful as delivery vehicles in vitro and in vivo. It has been shown that large unilamellar vesicles (LUV), which range in size from 0.2-4.0 µm can encapsulate a substantial percentage of an aqueous buffer containing large macromolecules. RNA, DNA, and intact virions can be encapsulated within the aqueous interior and be delivered to cells in a biologically active form (Fraley et al., Trends Biochem. Sci., 6:77, 1981). In order for a liposome to be an efficient gene transfer vehicle, the following characteristics should be present: (1) encapsulation of the nucleic acid of interest (i.e., a nucleic acid encoding a fusion polypeptide of the invention or a vector comprising the nucleic acid) at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino et al., Biotechniques, 6:682, 1988).

In another embodiment, the invention provides method for modulating epithelial cell proliferation in a subject. In one aspect, the modulating is by administering to the subject a fusion polypeptide comprising a collagen-binding domain source linked to an epithelial cell proliferation-modulating agent. In another aspect, the modulating is by administering to the subject a therapeutically effective amount of a nucleic acid sequence encoding a fusion polypeptide comprising a collagen-binding domain linked to an epithelial cell proliferation-modulating agent. The fusion polypeptide is valuable as a therapeutic in cases in which there is impaired healing of wounds or there is a need to augment normal healing mechanisms by facilitating tissue regeneration. For example, the method of the invention can be used in aiding tissue repair or regeneration at an ulcer site in a human or other subject.

"Modulation of epithelial cell proliferation" as used herein, refers to regulating or controlling epithelial cell growth. The condition can include both hypertrophic (the continual multiplication of cells resulting in an overgrowth of a cell population within a tissue) and hypotrophic (a lack or deficiency of cells within a tissue) cell growth or an excessive influx or migration of cells into an area of a body. The epithelial cell populations are not necessarily transformed, tumorigenic, or malignant cells, but can include normal cells as well.

The invention further provides a method for modulating tissue regeneration in a subject. In one aspect, the method comprises administering to the subject a therapeutically effective amount of a fusion polypeptide of the invention. In another aspect, the method comprises administering to the subject a therapeutically effective amount of a nucleic acid encoding a fusion polypeptide of the invention. Diseases, disorders or ailments modulated by a fusion polypeptide of the invention include tissue repair subsequent to traumatic injuries or conditions, including arthritis, osteoporosis and other skeletal disorders, and burns. Because these problems are due to a poor growth response of the fibroblasts, stem cells, chondrocytes, osteoblasts, or fibroblasts at the site of injury, the addition of an active biologic agent that stimulates or induces growth of these cells, particularly epithelial cells, is beneficial. The term "induce" or "induction" as used herein, refers to the activation, stimulation, enhancement, initiation, and/or maintenance of the cellular mechanisms or processes necessary for the formation of any of the tissue, repair process, or development, as described herein.

The compositions and methods of the invention are useful for revitalizing scar tissue resulting from injuries due to surgical procedures, irradiation, laceration, toxic chemicals, viral infection bacterial infection, or burns. The term "scar tissue" means fibrotic or collagenous tissue formed during the healing of a wound or other morbid process. For example, a fusion polypeptide of the invention can be included in a controlled release matrix that can be positioned in proximity to damaged tissue, thereby promoting regeneration of such tissue. The term "controlled release matrix" means any composition that allows the slow release of a bioactive substance that is mixed or admixed therein. The matrix can be a solid composition, a porous material, or a semi-solid gel, or liquid suspension containing bioactive substances. The term "bioactive material" means any composition that will modulate tissue repair when used in accordance with the method of the present invention. The bioactive materials/matrix can be introduced by means of injection, surgery, catheters, or any other means suitable for modulating tissue repair.

It is further envisioned that the method of the invention can be used to aid wound repair in guided tissue regeneration (GTR) procedures. Such procedures are currently used by those skilled in the medical arts to accelerate wound healing following invasive surgical procedures. Typically, nonresorbable or bioabsorbable membranes are used to accelerate wound healing by promoting the repopulation of the wound area with cells that form the architectural and structural matrix of the tissue. For example, the method of the invention can be used in aiding periodontal tissue regeneration in a human or lower animal by placing a composition containing a bioresorbable polymer, leachable solvent, and a fusion polypeptide, comprising a collagen-binding domain and an epithelial cell proliferation-modulating agent, at a site in need of periodontal tissue regeneration in a human or other mammal such that the composition is effective for aiding tissue regeneration by releasing a therapeutically-effective amount of the fusion polypeptide at the site.

In another aspect, the invention is useful for the purposes of promoting tissue growth during the process of tissue engineering. By "tissue engineering" is meant the creation, design, and fabrication of biological prosthetic devices, in combination with synthetic or natural materials, for the creation, augmentation, or replacement of body tissues and organs. Thus, the method can be used to augment the design and growth of tissue inside the body to repair or replace diseased or damaged tissue. A specific, non-limiting example is the use of a method of the invention in promoting the growth of skin graft replacements that are used as a therapy in the treatment of burns and ulcers. Thus, the invention further encompasses a tissue graft, comprising epithelial cells treated with a fusion polypeptide of the invention. Also provided is a method of preparing a tissue graft using an effective amount of a fusion polypeptide of the invention.

In another aspect of tissue engineering, a fusion polypeptide of the invention can be included in cell-containing or cell-free devices that induce the regeneration of functional human tissues when implanted at a site that requires regeneration. As previously discussed, biomaterial-guided tissue regeneration can be used to promote epithelial cell proliferation in, for example, digestive tract tissue for treatment of gastric ulcers or the pathogenic result of Krohn's disease. Thus, a fusion polypeptide of the invention can be used to promote the growth of reconstituted tissues assembled into three-dimensional configurations at the site of a wound or other tissue in need of such repair.

In another aspect of tissue engineering, a fusion polypeptide of the invention can be included in external or internal devices containing human tissues designed to replace the function of diseased internal tissues. This approach involves isolating cells from the body, placing them on or within structural matrices, and implanting the new system inside the body or using the system outside the body. The method of the invention can be included in such matrices to promote the growth of tissues contained in the matrices. For example, a fusion polypeptide of the invention can be included in a cell-lined vascular graft to promote the growth of the cells contained in the graft. It is envisioned that the method of the invention can be used to augment tissue repair, regeneration, and engineering in products, such as epithelial tissue, cartilage and bone, central nervous system tissues, muscle, liver, and pancreatic islet (insulin-producing) cells.

In another embodiment, the invention provides a pharmaceutical composition for promoting tissue repair. In one aspect, the composition comprises a fusion polypeptide, comprising a collagen-binding domain linked to an epithelial cell proliferation-modulating agent in a pharmaceutically acceptable carrier. In another aspect, the composition comprises a nucleic acid encoding a fusion polypeptide of the invention.

A pharmaceutical composition according to the invention can be prepared by placing a fusion polypetide of the invention, or nucleic acid sequence encoding a fusion polypeptide of the invention, into a form suitable for administration to a subject using carriers, excipients, and additives or auxiliaries. Generally, the terms "treating," "treatment," and the like are used herein to mean obtaining a desired pharmacologic and/or physiologic effect. The effect may be therapeutic in terms of a partial or complete cure for a cell proliferative disorder. "Treating" as used herein, covers any treatment, or prevention of tissue damage, or for ameliorating the pathogenic effect of a tissue regeneration disorder, such as tissue necrosis due to diabetes, in a mammal, particularly a human, and includes:

(a) preventing the disease from occurring in a subject that may be predisposed to the disease, but has not yet been diagnosed as having it;

(b) inhibiting the disorder, i.e., arresting the development of, for example, a tumor; or (c) relieving or ameliorating the disorder or disease, i.e., cause regression of the disorder or disease.

Thus, the invention includes various pharmaceutical compositions useful for ameliorating symptoms attributable to a tissue regeneration disorder or, alternatively, for inducing tissue regeneration following, for example, a surgical procedure. Pharmaceutical compositions of the invention are also useful for ameliorating the pathogenic effects of ulcers, for example, resulting in tissue damage.

A pharmaceutical composition according to the invention can be prepared to include a nucleic acid, or polypeptide encoded therefrom, into a form suitable for administration to a subject using carriers, excipients, and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol, and polyhydric alcohols. Intravenous vehicles include fluid and nutrient replenishers. Preservatives include antimicrobial, anti-oxidants, chelating agents, and inert gases. Other pharmaceutically acceptable carriers include aqueous solutions, non-toxic excipients, including salts, preservatives, buffers and the like, as described, for instance, in Remington's Pharmaceutical Sciences, 15th ed., Easton: Mack Publishing Co., 1405-1412, 1461-1487 (1975), and The National Formulary XIV., 14th ed., Washington: American Pharmaceutical Association (1975), the contents of which are hereby incorporated by reference. The pH and exact concentration of the various components of the pharmaceutical composition are adjusted according to routine skills in the art. See Goodman and Gilman's, The Pharmacological Basis for Therapeutics (7th ed.). The pharmaceutical compositions according to the invention may be administered locally or systemically. By "therapeutically effective dose" is meant the quantity of a compound according to the invention necessary to prevent, to cure, or at least partially arrest the symptoms of tissue damage. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Langer, Science, 249: 1527, (1990); Gilman et al. (eds.) (1990), each of which is herein incorporated by reference.

As used herein, "administering a therapeutically effective amount" is intended to include methods of giving or applying a pharmaceutical composition of the invention to a subject that allow the composition to perform its intended therapeutic function. The therapeutically effective amounts will vary according to factors, such as the degree of infection in a subject, the age, sex, and weight of the individual. Dosage regima can be adjusted to provide the optimum therapeutic response. For example, several divided doses can be administered daily or the dose can be proportionally reduced as indicated by the exigencies of the therapeutic situation.

The pharmaceutical composition can be administered in a convenient manner, such as by injection (subcutaneous, intravenous, etc.), oral administration, inhalation, transdermal application, or rectal administration. Depending on the route of administration, the pharmaceutical composition can be coated with a material to protect the pharmaceutical composition from the action of enzymes, acids, and other natural conditions that may inactivate the pharmaceutical composition. The pharmaceutical composition can also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersions. In all cases, the composition must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating, such as lecithin, by the maintenance of the required particle size, in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent that delays absorption, for example, aluminum monostearate and gelatin.

Sterile injectable solutions can be prepared by incorporating the pharmaceutical composition in the required amount in an appropriate solvent with one or a combination of ingredients enumerated above, as required, followed by filtered sterilization. Generally, dispersions are prepared by incorporating the pharmaceutical composition into a sterile vehicle that contains a basic dispersion medium and the required other ingredients from those enumerated above.

The pharmaceutical composition can be orally administered, for example, with an inert diluent or an assimilable edible carrier. The pharmaceutical composition and other ingredients can also be enclosed in a hard or soft-shell gelatin capsule, compressed into tablets, or incorporated directly into the individual's diet. For oral therapeutic administration, the pharmaceutical composition can be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations can, of course, be varied and can conveniently be between about 5% to about 80% of the weight of the unit.

The tablets, troches, pills, capsules, and the like can also contain the following: a binder, such as gum gragacanth, acacia, corn starch, or gelatin; excipients such as dicalcium phosphate; a disintegrating agent, such as corn starch, potato starch, alginic acid, and the like; a lubricant, such as magnesium stearate; and a sweetening agent, such as sucrose, lactose or saccharin, or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar, or both. A syrup or elixir can contain the agent, sucrose as a sweetening agent, methyl and propylparabens as preservatives, a dye, and flavoring, such as cherry or orange flavor. Of course, any material used in preparing any dosage unit form should be pharmaceutically pure and substantially non-toxic in the amounts employed. In addition, the pharmaceutical composition can be incorporated into sustained-release preparations and formulations.

Thus, a "pharmaceutically acceptable carrier" is intended to include solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the pharmaceutical composition, use thereof in the therapeutic compositions and methods of treatment is contemplated. Supplementary active compounds can also be incorporated into the compositions.

It is especially advantageous to formulate parenteral compositions in dosage unit form for ease of administration and uniformity of dosage. "Dosage unit form" as used herein, refers to physically discrete units suited as unitary dosages for the individual to be treated; each unit containing a predetermined quantity of pharmaceutical composition is calculated to produce the desired therapeutic effect in association with the required pharmaceutical carrier. The specification for the novel dosage unit forms of the invention are dictated by and directly dependent on: (a) the unique characteristics of the pharmaceutical composition and the particular therapeutic effect to be achieve, and (b) the limitations inherent in the art of compounding such an pharmaceutical composition for the treatment of a pathogenic infection in a subject.

The principal pharmaceutical composition is compounded for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

Material and Methods

Figure 2:
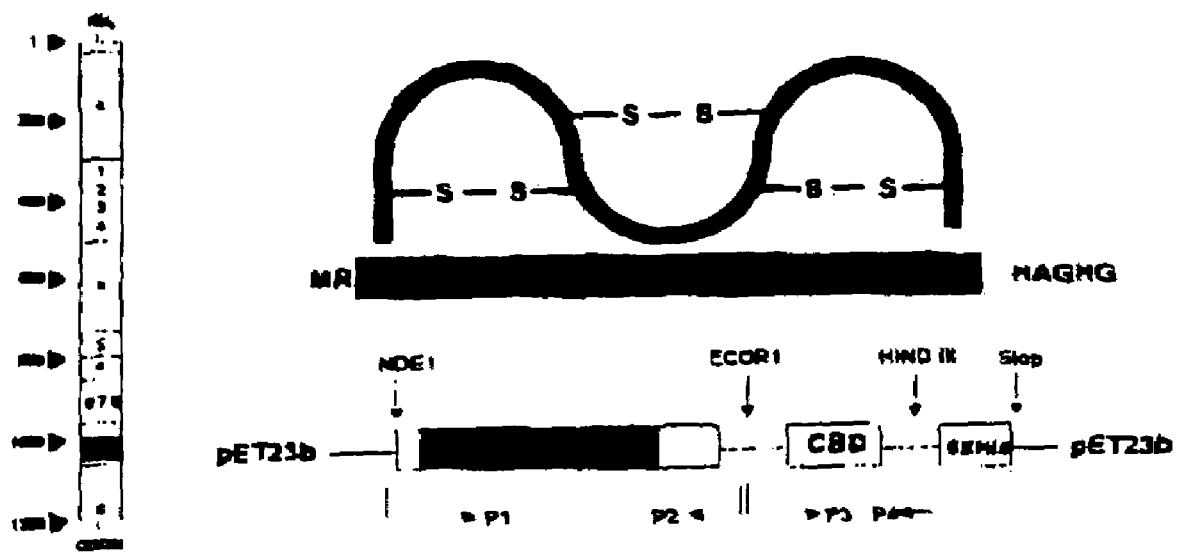
FIG. 2 is schematic diagram showing the design of recombinant EGF-CBD fusion proteins. Targeted congeners of epidermal growth factor consisting of a 6×His purification tag, an auxiliary von Willebrand factor-derived collagen-binding domain, and the cDNA sequence encoding the mature active fragment of human EGF (EGF 53+7 flanking amino acids) are shown (P1 sequences are listed as SEQ ID NOs:2 and 3; P2 sequences are listed as SEQ ID NOs:4 through 6; P3 sequences are listed as SEQ ID NOs:7 and 8; P4 sequences are listed as SEQ ID NOs:9 through 11).

Molecular Engineering And Cloning Of The Expression Plasmids. FIG. 1 shows diagrammatically the structural domains of von Willebrand Factor (vWF), identifying the primary collagen-binding domain (CBD) within the A1 loop of the mature polypeptide. The mimimal collagen binding amino acid sequences of human and bovine vWF, including the flanking residues, are shown. The mature EGF polypeptide, consisting of 53 amino acids, is generated from a large transmembrane precursor protein by proteolytic cleavage (FIG. 2). In engineering the EGF-CBD fusion proteins, human coding sequences of EGF, including two additional residues at the N-terminal end and 5 amino acids at the C-terminal end of the protein were utilized. This design not only retains the original (physiological) cleavage sites, but includes these native flanking residues in an effort to facilitate the renaturation of the recombinant protein. The extended C-terminal residues (H-A-G-H-G; SEQ ID NO:5), in particular, are considered to be important design considerations in that they are very similar to the N-terminal sequences flanking the native vWF CBD (see FIG. 1). Therefore, this design is intended to optimize both the refolding of the recombinant fusion protein and the presentation of the collagen-binding domain (CBD) in solution. Moreover, the retention of the natural proteolytic cleavage site between the growth factor and the intrinsic CBD are intended to provide a mechanism for enzymatic release (i.e., "time release") of the soluble growth factor to enhance its physiological efficacy and potential therapeutic utility.

The rEGF and rEGF-CBD fusion proteins were cloned into pET expression vectors (Novagen) suitable for high-level expression in *E. coli* (FIG. 2). A strategically modified collagen-binding decapeptide derived from a functional domain within bovine von Willebrand factor (vWF;CBD; FIG. 1) which normally functions in the recognition of exposed vascular collagen was utilized. A cysteine residue within the original vWF decapeptide sequence was replaced conservatively by a methionine, in order that this auxiliary domain would not interfere with the elaborate disulfide bond formation required for the folding and/or renaturation of the recombinant growth factor. Flanking linkers were also specifically designed: (i) to be devoid of native Cys residues, (ii) to include glycine residues to increase rotational flexibility and to minimize stearic hindrances, and (iii) a histidine residue was included to promote an external configuration of the collagen-binding domain within the context of the homodimeric fusion protein. Thus, the design of the EGF-CBD fusion constructs, which incorporate the collagen binding decapeptide WREPSFMALS (SEQ ID NO:1) (bovine sequence) into the EGF fusion protein, was intended for targeting the biologically active growth factor to collagen exposed by injury, inflammation, ulcers, or reparative surgical procedures.

Expression, Purification, and Renaturation of regf Fusion Proteins. The rEGF and rEGF-CBD constructs were generated from human cDNA by RT-PCR. PCR products were initially ligated into TA cloning vectors, and the sequences were confirmed by direct DNA sequencing. Upon confirmation of the correct DNA sequences, the respective inserts, including linker sequences, were released by enzymatic digestion and cloned into a pET expression vector (Novagen), transformed into competent cells (BL21 DE3 strain of *E. coli*), and protein expression was initiated by the addition of IPTG to the culture medium. The expressed fusion proteins were isolated from *E. coli* inclusion bodies, solubilized with 8M urea, purified to near homogeneity under denaturing conditions (8M urea) using nickel chelate chromatography, and renatured by oxidative refolding under optimized redox conditions.

Assessment of the Collagen-Binding Properties of regf Fusion Proteins. The collagen-targeted or non-targeted rEGF was applied onto standard ELISA plates coated with type I collagen (vitrogen-100). The plates were washed 3× with PBS, and the bound fusion protein was detected by immunohistochemical methods, using a primary antibody directed against the His×6 tag (Santa Cruz SC-804) and a HRP-labeled secondary antibody (Pierce 3146022). The calorimetric peroxidase reaction was initiated by the addition of TMB as a substrate.

Assessment of Biological Activity of the Recombinant EGF Bearing a Collagen-binding Domain. The mitogenic activity of the recombinant EGF fusion proteins were determined by calorimetric immuoassay of cell proliferation (Boehringer Mannheim), based on the measurement of BrdU incorporation during DNA synthesis, and using purified commerical EGF as standardized control. Briefly, murine NIH3T3 fibroblasts (2×104 cells/well) in 96-well microtiter plates in 0.1 ml DMEM supplemented with 5% fetal bovine serum (D5 medium). The cells were cultured for 3 to 4 days until confluent, at which time dilutions of samples containing EGF were added to the cell cultures, as described by George Nascimento et al., with the exception that BrdU (10 mM) is added in place of [3H] thymidine approximately 18 hours (10-24 hours) later. After a final incubation for 24 hours, the labeling media was removed, the cells were fixed, and the incorporation of BrdU was detected by peroxidase-conjugated anti-BrdU Fab-fragments, utilizing TMB as a substrate. Each sample was assayed in triplicate wells, utilizing commercial EGF (Sigma Chemical Co., St. Louis, Mo.) as a pharmacological standard. The results were quantified by measuring the absorbance at 620 nm using a scanning multiwell spectrophometer (Phoenix).

In Vivo Binding of the rEGF-CBD Fusion Protein to Colonic Mucosa in a Nude Mouse Model of Experimental Colitis. In compliance with an animal protocol approved by the USC Institution Animal Care and Use Committee, six-week old athymic nude mice weighing between 20-25 g were anesthetized by inhalation with methoxyflurane to effect. On Day 1, a polyetheylene tubing (4 cm long;I.D. 0.011", O.D. 0.024", Becton Dickinson, attached to a 32 G needle with 1 ml syringe) was inserted into the rectum of each mouse to a depth of 2 cm. Two PBS enemas (0.5 ml each) were given to empty the colon of fecal material, after which 0.5 ml of 5% acetic acid enemas were given. The catheters were removed and the mice were then allowed to recover under a warming lamp, and returned to their cages. Twenty-four hours (Day 2) after the induction of colitis, two PBS enemas were again administered to remove fecal material. Then, 0.5 ml of either PBS control, EGF or EGF-CBD (each 10 mg/ml), was given by enema. Thirty minutes later, the animals were sacrificed, the colon harvested, and processed for immunohistochemical staining. The bound fusion protein was detected in tissue sections of colon by immunohistochemical methods, using a primary antibody directed against the His×6 tag and an HRP-labeled secondary antibody as described above. The calorimetric reaction was initiated by the addition of TMB as a substrate. Bound immunoreactive EGF was detected by accumulation of reddish-brown staining material on the luminal surface of injured colonic segments.

Efficacy of Collagen-targeted EGF (EGF-CBD) in a Nude Mouse Model of Experimental Colitis. Induction of colitis in athymic mice was conducted, as described above. For these experiments, the mice were sacrificed 24 hours (Day 3) after treatment with PBS, EGF, or EGF-CBD. The colons were extracted, washed 3 times with PBS, and fixed in 10% formalin. Tissue sections from formalin-fixed colonic segments were stained with hematoxylin-eosin or Mason trichrome stain for collagen and examined under light microscopy to determine the extent of edema, hemorrhage, inflammation, the number of well-formed colonic villi, and presence of overt stem cell proliferation. Histologic grading of severity of colitis was conducted by an observer blinded to the treatment group by morphometric analysis using an Optimas image analysis system.

Results

The present invention provides a composition and method for tethering an appropriately engineered recombinant fusion polypeptide displaying a high affinity collagen-binding domain derived from von Willebrand factor (FIG. 1) linked to an epithelial cell proliferation agent to sites of exposed collagen, such as those that occur at the site of a wound or lesion. The composition improves the biologic effects of, for example, EGF in an animal model of experimental colitis by cytoprotection and by modulating the proliferation of stem cells located within the colonic crypts.

Figure 3:
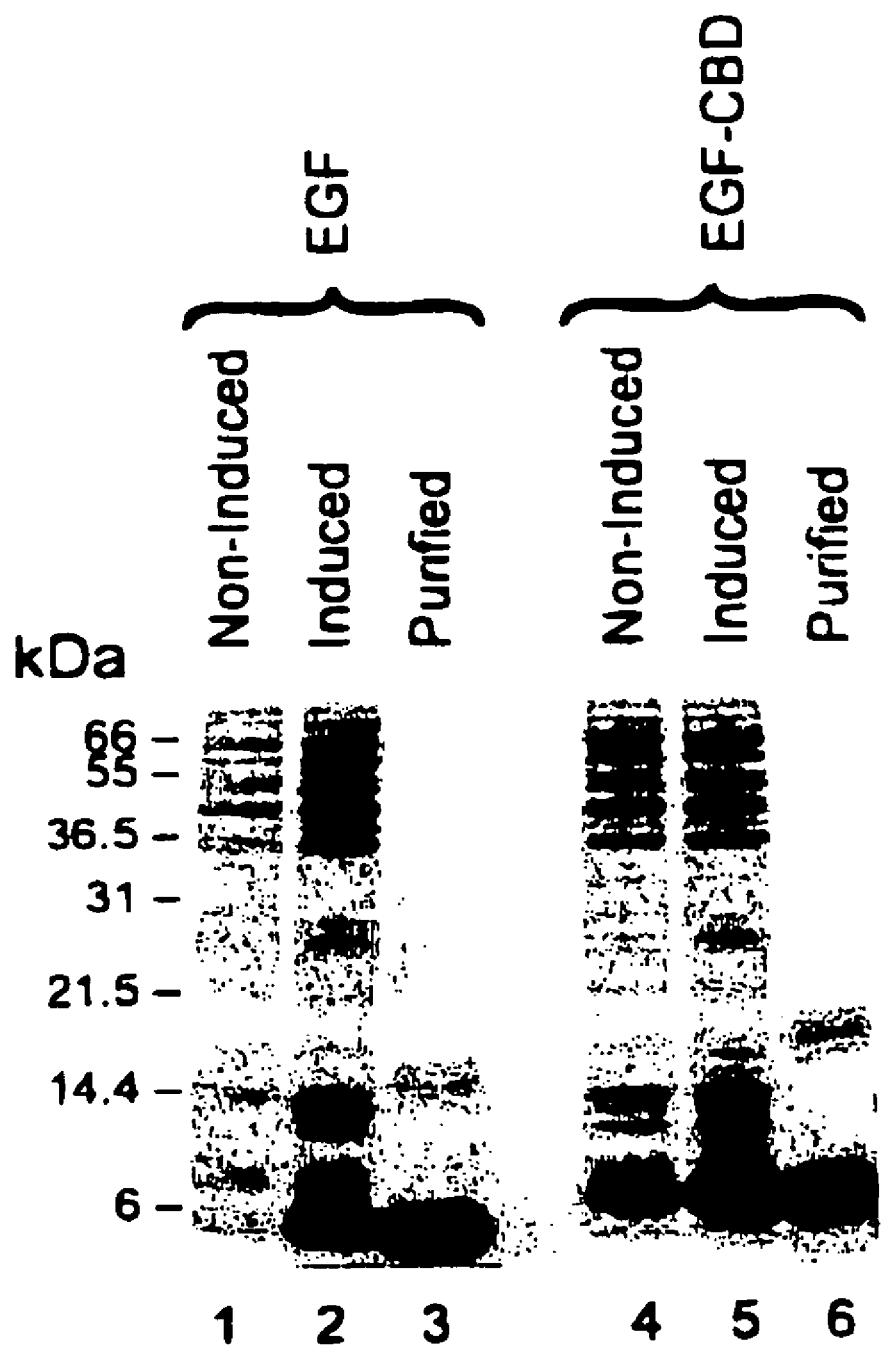
FIG. 3 shows the expression, induction and purification of an EGF fusion protein displaying a collagen-binding domain. Coomassie blue-stained gels identify EGF bands at molecular weight ~6 kDa for both collagen-targeted (EGF-CBD) and non-targeted (EGF) epidermal growth factor.

As shown in FIG. 3, the EGF-CBD fusion protein was produced at high levels (recovery was ~80 to 100 mg /1 L bacterial culture) and purified to near homogeneity by metal chelate chromatography, as determined by SDS-PAGE (see Lanes 3 and 6). The fusion polypeptide can be solubilized by 6M guanidinium HCl or 8M urea, respectively, and renatured under carefully controlled redox conditions to yield a soluble, renatured polypeptide. Under optimal conditions, the bulk (>50%) of the purified recombinant protein was effectively renatured and recovered in soluble form. Further studies examined the physicochemical conditions of protein renaturation, including the yield (% recovery) of renatured proteins at various protein concentrations and the stabilizing effects of additives (such as sucrose or glycerol) observed upon withdrawal (dialysis) of the denaturants. These studies determined that optimal protein refolding is achieved at protein concentrations of <0.5 mg/ml, and that 20% sucrose is beneficial in optimizing the recovery of the renatured protein.

To assess the collagen-binding affinity of the rEGF-CBD fusion protein, the collagen-targeted or non-targeted rEGF was applied to collagen-coated ELISA plates and subjected to stringent washing conditions. As shown in FIG. 4, the collagen-targeted EGF (EGF-CBD) exhibited enhanced binding affinity to collagen matrices compared to non-targeted EGF or PBS, demonstrating that this gain-of-function phenotype is evident and may be used to distinct advantage in animal models of wound healing. The biologic activity of the collagen-targeted rEGF-CBD, as well as the rEGF protein, was evaluated by in vitro cell proliferation assays using human foreskin fibroblasts and purified commercial EGF as a standardized control. Under the experimental conditions described above by BrdU incorporation assays, dose-dependent stimulation of cell growth was observed with the commercial EGF with maximal stimulation observed at 20 ng/ml.

Figure 5:
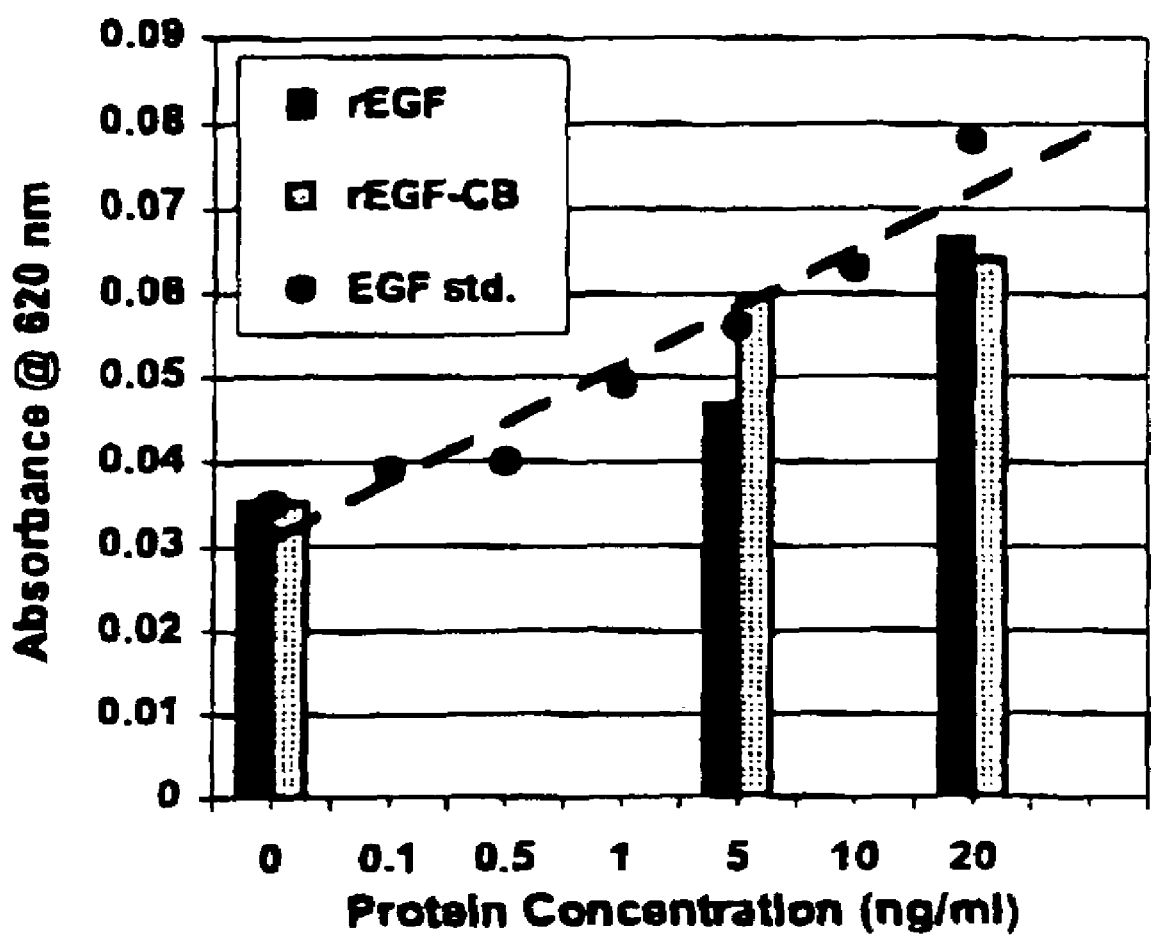

As shown in FIG. 5, the specific biological activity of each construct (rEGF and rEGF-CBD), tested at 5 ng/ml was found to be nearly 90% as active (overall mean specific activity=>75%) as the commercial standard, indicating that the renatured EGF fusion proteins were not only refolded into soluble growth factors, but were demonstrably biologically active.

Figure 6:
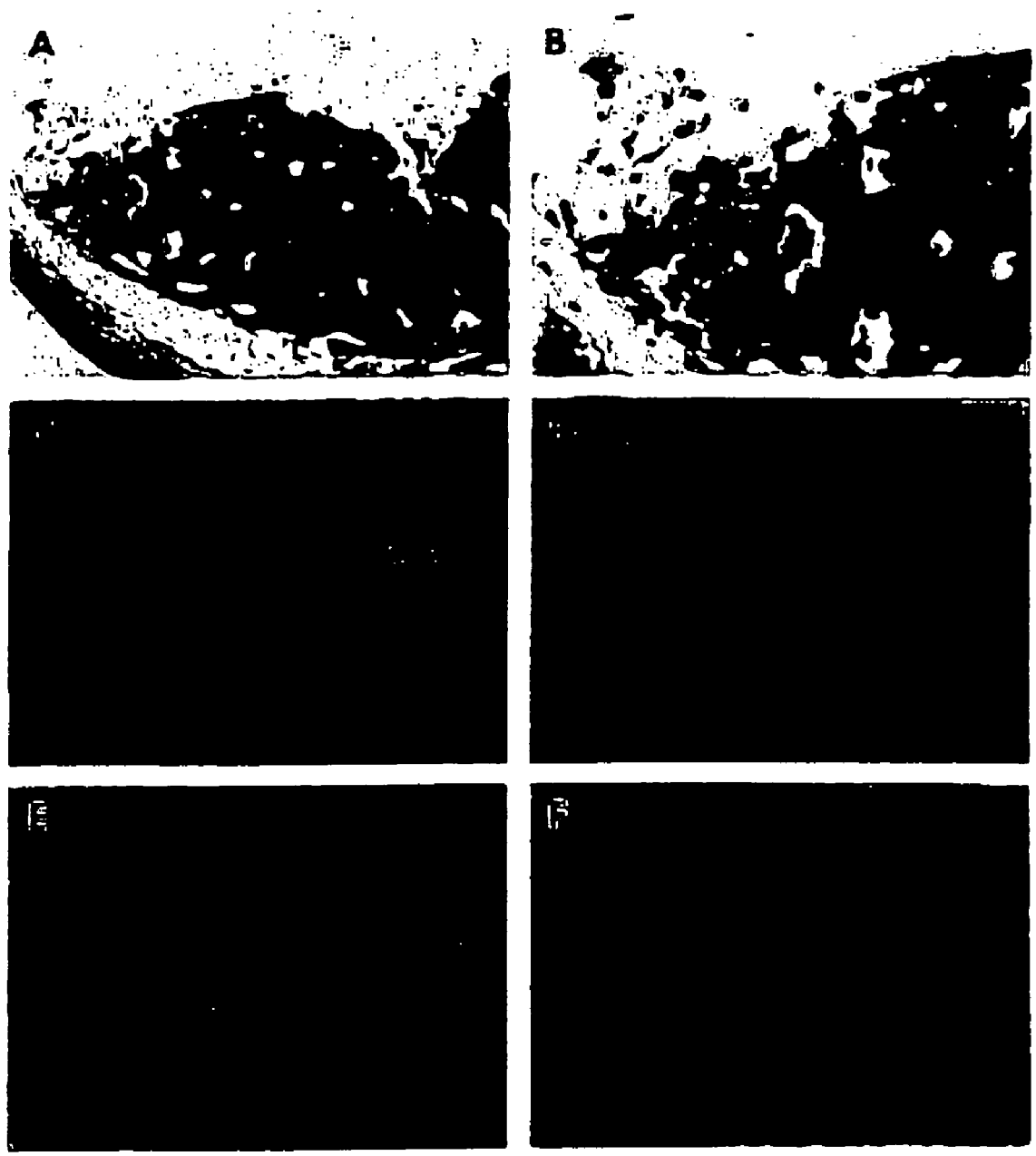

In vivo binding studies of EGF-CBD vs EGF or PBS control to exposed collagen in a nude mouse model of experimental colitis were conducted (FIG. 6). Mason trichrome staining of tissue sections from colonic segments revealed significant areas of exposed collagen (FIGS. 6A & 6B). The EGF-CBD fusion protein was bound to and accumulated at areas of exposed collagen within colonic erosion, as indicated by positive immunostaining (brown-staining material; FIGS. 6C & 6D) using a primary antibody directed against the His×6 tag. In contrast, immunostaining of the inflamed bowel treated with non-targeted EGF (FIG. 6E) or PBS (FIG. 6F) was minimal to negative, indicating that the non-targeted EGF did not adhere to the injured mucosa, and was effectively washed away by subsequent PBS infusions.

Figure 7:
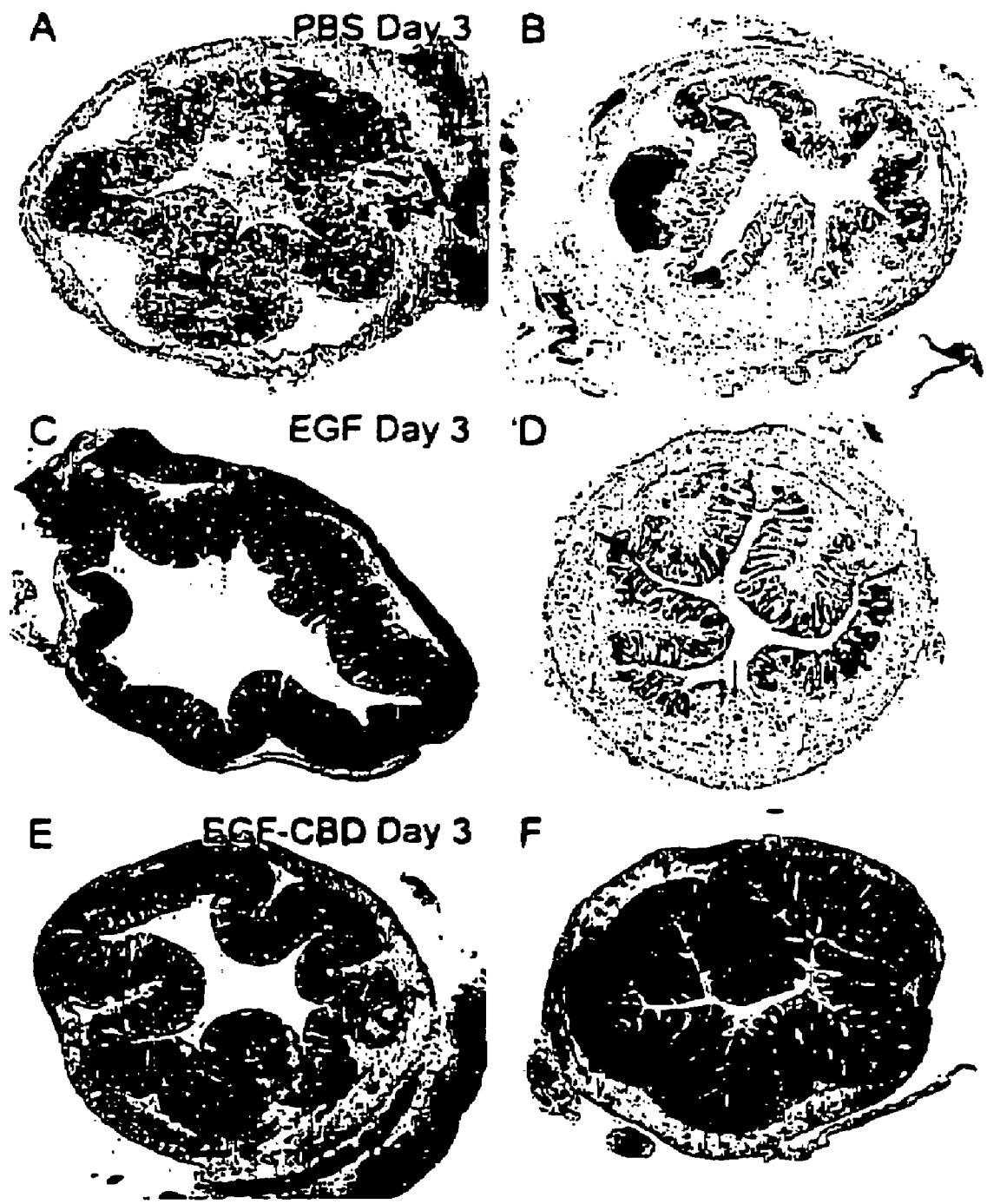

In the animal model of experimental colitis, tissue sections of colon from PBS control-treated mice (FIG. 7A & B) showed extensive ulceration, and significant bleeding, edema, ulceration and acute inflammation on Day 3. While some beneficial effects were observed with the non-targeted EGF (see FIG. 7C & D), the number of well-formed crypts was not significantly increased compared to the PBS group. In contrast, colonic tissue sections from EGF-CBD-treated mice (FIG. 6; Table 1) showed complete regeneration of intestinal crypts, with focal areas of inflammation and ulceration and minimal bleeding. Additionally, a number of crypts showed intense stem cell proliferation, providing evidence of intestinal regeneration as well as remarkable cytoprotection.

TABLE 1

Histologic Evaluation Of Colitis By Morphometric Analysis (Optimas)

| Variable | None | PBS* | EGF** | EGF-CBD |
|---|---|---|---|---|
| Total, mm$^2$ | 3.4 ± 0.7 | 4.9 ± 1.0 | 3.0 ± 1.2 *p = 0.02 | 2.9 ± 0.7 *p = 0.006 **p = 0.473 |
| Lumen, mm$^2$ | 0.4 ± 0.2 | 1.6 ± 0.8 | 0.4 ± 0.1 *p = 0.031 | 0.2 ± 0.2 *p = 0.015 **p = 0.173 |
| Wall, mm$^2$ | 3.0 ± 0.8 | 3.4 ± 0.4 | 2.6 ± 1.2 *p = 0.142 | 2.7 ± 0.8 *p = 0.097 **p = 0.441 |
| Bleeding, % | 1.6 ± 1.9 | 2.3 ± 2.0 | 0.5 ± 0.7 *p = .066 | 0.07 ± 0.14 *p = 0.036 **p = 0.112 |
| Edema, % | 8.8 ± 3.3 | 5.6 ± 4.3 | 5.3 ± 3.0 *p = .446 | 3.9 ± 4.1 *p = 0.28 **p = 0.310 |
| Ulceration, % | 41.3 ± 14.3 | 67.0 ± 39.5 | 33.2 ± 32.8 *p = 0.102 | 3.6 ± 7.2 *p = 0.012 **p = 0.064 |
| Inflammation, % | 8.8 ± 4.8 | 9.9 ± 11.0 | 5.8 ± 6.1 *p = .249 | 0.2 ± 0.4 *p = 0.059 **p = 0.059 |
| # of Crypts | 34.8 ± 11.4 | 24.0 ± 22.9 | 52.2 ± 29.8 *p = 0.085 | 89.2 ± 8.1 *p = 0.001 **p = 0.027 |

*p = compared to PBS (no. of crypts: EGF-CBD > PBS: bleeding and ulceration: EGF-CBD < PBS
**p = compared to EGF (no. of crypts: EGF-CBD > EGF); n = 4 each group (except for PBS n = 5)

The studies presented herein clearly indicate that the collagen-binding function of the fusion polypeptide of the invention can effect a major and significant improvement in the rate and extent of wound healing in general. The invention is useful for targeting a pharmaceutical agent to a site of epithelial tissue damage such that repair of the damaged tissue is enhanced. The invention encompasses the treatment of disorders associated with epithelial tissue damage, such as damage to lung tissue or skin tissue. Though not limited to the following example, it is believed that the present fusion polypeptide will be particularly useful in the repair of digestive tract-associated lesions.

Inflammatory bowel disease, encompassing ulcerative colitis and Crohn's disease (regional enteritis), are prominent causes of chronic illness in Western Europe and North America. Recently, modulation of cytokines (by IL-10 and TGF-β) that are important in the normal homeostasis of the gut immune system have been investigated in the pathogenesis and treatment of experimental colitis. Conceivably, multi-modal therapies, which include anti-inflammatory activities, cytoprotective effects, and epithelial cell re-population strategies will be more effective in attenuating or reducing the severity of inflammatory bowel disease.

EGF has been shown to be a stimulator of epithelial cell proliferation in the human intestine. In patients with Zollinger-Ellison syndrome, a beneficial effect of EGF in reducing gastric secretion has been reported, although the use of EGF was not shown to be as effective as proton-pump inhibitors and histamine H2-receptor blockers. In another clinical trial for gastric ulcers, patients who received intravenously administered EGF showed an increased ulcer healing rate compared to the placebo control group (Matsuo et al., Hellenic J Gastroenterol, 5(suppl 1):217, 1992). Clinical evidence of the efficacy of intravenous EGF in an infant with necrotizing enterocolitis and in children with congenital microvillus atrophy has also been reported (Guglietta et al., Eur. J. Gastroenterol. Hepatol., 7:945, 1995). However, to date, there has been no clinical trials or reports of efficacy for colonic instillation of recombinant EGF.

In animal models, preclinical studies on the efficacy of EGF in trinitrobenzenesulfonic acid/ethanol (TNBS)-induced colitis in immunocompetent rats have been conducted. In these studies, systemic EGF administration reduced mucosal damage and inflammation when EGF was given intraperitoneally before, but not after, the induction of colitis, revealing a significant cytoprotective effect. In another study, systemic but not intracolonic administration of EGF was reported to accelerate the healing of colonic ulcerations in a similar model of experimental colitis. The present invention provides a novel fusion polypeptide for the local delivery of an epithelial cell proliferation-modulating agent, such as EGF, to a wound site, such as damaged intestinal epithelium, by enhanced binding of EGF to extracellular matrix molecules, specifically, to exposed collagen. Mature EGF protein was engineered to incorporate a high-affinity collagen-binding domain derived from von Willebrand factor into the primary structure of recombinant EGF fusion proteins, to specifically target EGF to sites of acute mucosal injury. This concept is based on von Willebrand factor's demonstrable surveillance function in targeting platelets to vascular lesions. Further, vWF-derived collagen-binding domains can be used to modulate the biologic activity and/or to target the TGF-β family of growth factors for specific wound healing applications.

Recently, a collagen-binding domain derived from a prokaryotic collagenase was fused to an EGF polypeptide (Nishi et al., Proc. Natl. Acad. Sci. USA, 95:7018, 1998). The recombinant fusion protein was capable of binding to exposed collagen, but was devoid of any biologic activity associated with EGF (i.e., cell proliferation modulation). The loss of biologic activity may be due to interference of the auxiliary collagen-binding domain with EGF receptor binding or with the refolding of the fusion protein during renaturation. In contrast, the EGF-CBD fusion proteins presented herein incorporate several design features that have contributed to its functional activity. The composite EGF fusion protein of the present invention embodied several aspects of molecular engineering that may indeed be critical for determining biological activity. The amino acid sequence of the fusion protein was modified by replacing several problematic cysteine residues with methionine residues (see FIG. 2). In addition, flanking linkers were added to increase flexibility and to optimize the presentation of the collagen-binding domain. The aforementioned modifications yielded a fusion polypeptide with intrinsic collagen binding and growth factor activities. The EGF-CBD fusion protein was expressed at high levels in E.coli, purified to near homogeneity by metal chelate chromatography, and was renatured by oxidative refolding into a soluble, biologically active growth factor. In solid-state assays, the collagen-targeted EGF (EGF-CBD) exhibited enhanced binding affinity to collagen matrices compared to non-targeted EGF. Further, in vivo binding studies in an animal model of experimental colitis showed that the collagen-targeted EGF-CBD fusion protein, but not the non-targeted EGF, and accumulated at areas of inflamed and/or ulcerated colon. Finally, the EGF-CBD fusion protein not only exhibited mitogenic activity on NIH3T3 cells in vitro, but also demonstrated efficacy and upon intracolonic instillation, promoted healing of the inflamed colon in vivo at a faster rate than non-targeted EGF. These results provide an important proof of principle that an intrinsic collagen-binding domain can be incorporated into the primary structure of EGF to regulate and, indeed, to optimize its distribution to target tissues. An appealing concept is that the display of a collagen-binding domain on the EGF protein enabled binding of the EGF fusion protein to exposed collagen at the sites of colonic erosions, and that the tethering of EGF molecules in the vicinity of colonic stem cells stimulated mitotic activity and stem cell proliferation, resulting in both cytoprotective effects and enhanced rate of regeneration of the intestinal villi. The present invention provides a therapeutically useful fusion polypeptide for targeting damaged tissue for enhanced repair and represents a viable strategy for improved delivery of a pharmaceutical agent to damaged tissue. Clinical applications of this collagen-targeted EGF fusion protein include not only the promotion of healing of colonic lesions, for example, but also stimulation of wound healing in general, capture and expansion of crypt stem cells, and enhancement of retroviral gene transfer efficiency in colonic mucosal cells.

A number of embodiments of the invention have been described. Nevertheless, it will be understood that various modifications may be made without departing from the spirit and scope of the invention. Accordingly, other embodiments are within the scope of the following claims.

What is claimed is:

1. A fusion polypeptide comprising a collagen-binding domain and an epithelial cell proliferation-modulating agent, wherein:

the epithelial cell proliferation-modulating agent is selected from the group consisting of insulin, nerve growth factor (NGF), NGF receptor, epidermal growth factor (EGF) receptor, neu, wnt-2, and hepatocyte growth factor (HGF) receptor (c-met); and the collagen-binding domain is a collagen-binding domain of von Willebrand factor.

2. The fusion polypeptide of claim 1, wherein the collagen-binding domain of von Willebrand factor comprises the decapeptide WREPSFMALS (SEQ ID NO:1).

* * * * *

UNITED STATES PATENT AND TRADEMARK OFFICE
CERTIFICATE OF CORRECTION

PATENT NO. : 7,459,541 B2
APPLICATION NO. : 10/733852
DATED : December 2, 2008
INVENTOR(S) : Hall et al.

It is certified that error appears in the above-identified patent and that said Letters Patent is hereby corrected as shown below:

On the title page,

[*] Notice: Subject to any disclaimer, the term of this patent is extended or adjusted under 35 USC 154(b) by (612) days.

Delete the phrase "by 612 days" and insert -- by 607 days --

Signed and Sealed this

Twenty-fifth Day of August, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,459,541 B2 | Page 1 of 1 |
| APPLICATION NO. | : 10/733852 | |
| DATED | : December 2, 2008 | |
| INVENTOR(S) | : Hall et al. | |

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by 612 days.

Delete the phrase "by 612 days" and insert -- by 907 days --

Signed and Sealed this

Eighteenth Day of May, 2010

David J. Kappos
*Director of the United States Patent and Trademark Office*